United States Patent
Kronekvist

(10) Patent No.: US 6,302,104 B1
(45) Date of Patent: Oct. 16, 2001

(54) INTERLOCK ARRANGEMENT FOR EVAPORATORS IN AN ANESTHESIA APPARATUS

(75) Inventor: Hans Kronekvist, Stockholm (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 09/136,019

(22) Filed: Aug. 19, 1998

(30) Foreign Application Priority Data

Aug. 21, 1997 (SE) ............................................... 9703015

(51) Int. Cl.$^7$ ................................................. A61M 16/00
(52) U.S. Cl. ............................. 128/203.12; 128/200.19; 128/204.14; 128/205.24
(58) Field of Search ..................... 128/203.12, 202.22, 128/200.14, 200.19, 203.14, 204.13, 204.14, 205.24

(56) References Cited

U.S. PATENT DOCUMENTS

| | | | | |
|---|---|---|---|---|
| 698,898 | * | 4/1902 | Boekel | 128/200.19 |
| 703,611 | * | 7/1902 | Robertson | 128/200.19 |
| 1,216,285 | * | 2/1917 | Cash | 128/203.12 |
| 3,703,172 | * | 11/1972 | Hay . | |
| 4,058,120 | | 11/1977 | Caparelli et al. . | |
| 4,307,718 | | 12/1981 | Schreiber . | |
| 4,308,865 | * | 1/1982 | Hay | 128/200.14 |
| 4,434,790 | | 3/1984 | Olesen . | |
| 4,493,318 | * | 1/1985 | Mohr et al. | 128/200.19 |
| 5,537,992 | * | 7/1996 | Bjoernstijerna et al. | 128/203.14 |
| 5,921,235 | * | 7/1999 | Kronekvist | 128/203.12 |

FOREIGN PATENT DOCUMENTS 0 376 649  4/1990  (EP) .
507 899  7/1998  (SE) .

* cited by examiner

Primary Examiner—John G. Weiss
Assistant Examiner—V. Srivastava
(74) Attorney, Agent, or Firm—Schiff Hardin & Waite

(57) ABSTRACT

An interlock arrangement for evaporators in an anesthesia apparatus having at least two evaporators for setting a desired gas concentration prevents more than one evaporator from being activated at a time. The evaporators are connectable to a gas distributor. The interlock arrangement has for each evaporator, a mechanical element with the mechanical elements being arranged so that they cross each other in a crossing region. The mechanical elements are fashioned in the crossing region so that the mechanical element for one evaporator is displaced when this evaporator is activated and thereby locks the other mechanical elements in a position in which an activation of the further evaporators is prevented.

15 Claims, 4 Drawing Sheets

INTERLOCK ARRANGEMENT FOR EVAPORATORS IN AN ANESTHESIA APPARATUS

BACKGROUND OF THE INVENTION

1. Field of the Invention

The present invention is directed to an interlock arrangement for evaporators in an anesthesia apparatus, the anesthesia apparatus being of the type having at least two evaporators connectable to a gas distributor for setting a desired gas concentration as well as means for preventing more than one evaporator from being activated at a time.

2. Description of the Prior Art and Related Application

An anesthesia apparatus is disclosed in the Swedish Patent No. 507 899 having at least two evaporators for setting a desired gas concentration and a valve belonging to each evaporator, the valve controlling the gas flow through the respective evaporator, as well as means for enabling an opening and a closing of the valves that simultaneously prevent more than one evaporator from being activated. The evaporators and the valves are connectable to a gas distributor.

This anesthesia apparatus is provided with an evaporator carousel forming the gas distributor or the holder for the evaporators and valves and a gas supply unit, the gas distributor being rotatable relative to the gas supply unit. As a result, it is simple for a physician to change position relative to the patient and nonetheless have control over which evaporator is activated and what anesthesia concentration has been set at the active evaporator. As needed, the anesthesiologist can change the concentration of the anesthetic despite changing work positions, by rotating the gas distributor or holder, so that the activated evaporator is in a good position for the change in the concentration that has been set. In order to avoid having more than one evaporator activated at the same time, these applications state that an interlock arrangement is present, but details of such an interlock arrangement are not disclosed in detail in these applications.

U.S. Pat. No. 4,307,718 discloses an interlock arrangement for two evaporators arranged side-by-side in an anesthesia apparatus. Each evaporator has a cylindrical container with a rotary dial thereon as a cover, which is also used for setting the vapor concentration. Each adjustment dial has a recess at the cylindrical peripheral surface thereof. The interlock arrangement is formed by an arm which is pivotable around a shaft, the arm being provided with an outwardly directed pin arranged at each end, and the pins can be brought into engagement with the recesses. When the arm is pivoted into a position in which one pin is in engagement with the recess of one adjustment dial and closes this evaporator, the other evaporator can be set into a desired position, and vice versa. Such an interlock arrangement is exclusively limited to two evaporators.

SUMMARY OF THE INVENTION

An object of the present invention is to interlock arrangement of the type initially described, particularly for use in conjunction with an evaporator carousel with a plurality of evaporators, which assures that only one evaporator can be set at a time, in a way that is simple and dependable for the user.

The above object is achieved in accordance with the principles of the present invention in an anesthesia apparatus having at least two evaporators, with each evaporator being provided with a mechanical element which is actuated when that evaporator is activated, the respective mechanical elements of the evaporators crossing each other in a crossing region and interacting with each other in the crossing region so that when one of the mechanical elements is actuated upon activation of its associated evaporator, that mechanical element is placed in a position which locks the other mechanical elements and thereby prevents activation of any other evaporator.

The above object is also achieved in an anesthesia apparatus having a plurality of evaporators, with each evaporator having a valve associated therewith which is opened and closed to activate that evaporator, and wherein each evaporator has a mechanical element associated therewith which is actuated when the evaporator is activated by opening its valve. The respective mechanical elements of the evaporators cross each other in a crossing region and interact with each other in the crossing region so that when one mechanical element is actuated by opening the valve of the evaporator associated therewith, the actuated mechanical element forces the other mechanical elements into respective positions so that the respective valves of the other evaporators associated therewith are closed, and activation of any of the other evaporators is thereby prevented.

In an embodiment of the invention the evaporators with the appertaining valves are arranged exactly opposite one another. As a result, the shape of the mechanical elements can be comparatively simple and inexpensive to manufacture.

Preferably, each mechanical element is composed of at least one slide. To allow the interlock arrangement to be more easily assembled during production, it can be advantageous for each mechanical element to be composed of two slides that lie in axial alignment with one another. As used herein, therefore, the term "mechanical element" means a single part, or two parts acting together as a single part.

The slides can be shaped such that they can intermesh with one another in the crossing region. This allows the ends of the various slides to lie in approximately the same plane, which means that all evaporators and valves can be attached to the gas distributor at the same height.

In another embodiment of the invention at least three evaporators are arranged at the gas distributor and each of the slides has a trapezoidal shoulder that is disposed in a plane in the crossing region and which has an obtuse end directed toward an imaginary central point in the crossing region. When an evaporator is activated, the slide for this evaporator is displaced along its longitudinal direction, and thus the shoulder is displaced toward the central point into a position in which this shoulder locks or blocks the other shoulders and thus prevents the remaining slides from being capable of being displaced into an active evaporator position. As a result, an interlock arrangement is established that, in a way that is dependable for the user, assures that only one evaporator can be regulated at a time, even in conjunction with three or more evaporators.

DESCRIPTION OF THE PREFERRED EMBODIMENTS

Figure 1:
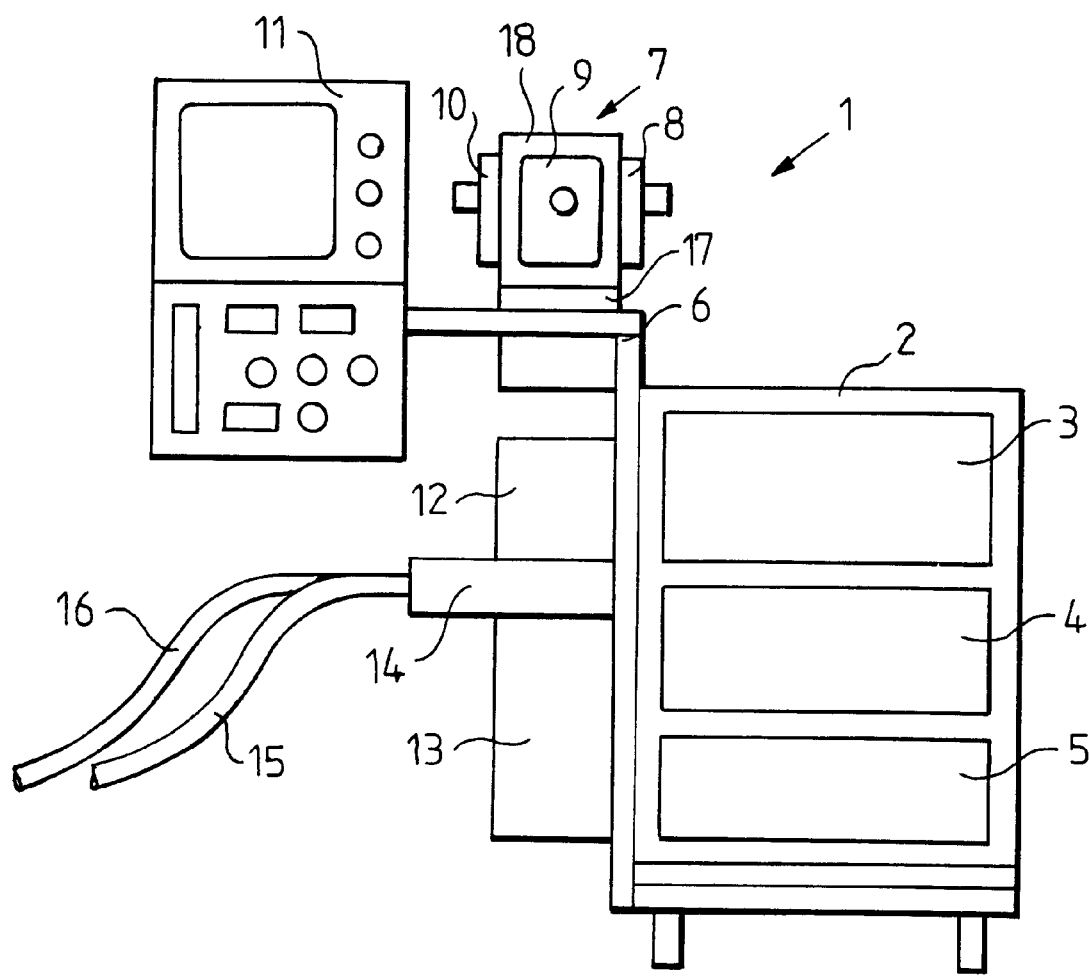
FIG. 1 is a schematic illustration of an anesthesia apparatus with an evaporator carousel in which the inventive interlock system can be employed.

FIG. 1 shows an anesthesia apparatus 1 that has a carriage 2 with a pneumatic unit 3 for gas-regulating equipment, an electronic unit 4 for electronic equipment, as well as a protection unit 5 for a back-up battery in case an interruption of power occurs. A stand 6 containing gas and signal lines is provided at the carriage 2. An evaporator carousel 7 is arranged at the stand 6. The evaporator carousel 7 is provided with a first evaporator 8, a second evaporator 9 as well as a third evaporator 10 that can contain the same or different anesthetics.

A control and monitoring unit 11 is arranged at the stand 6. Further, a bellows unit 12 and an absorber 13 are connected to a patient cassette 14 at the stand 6. An inspiration tube 15 and an expiration tube 16 proceed from the patient cassette 14, these being adopted for connection via a Y-section or the like to the patient being anaesthetized.

The evaporator carousel 7 has a gas supply unit 17 and a holder or a gas distributor 18 (hereinafter referred to only as a holder). Together with the evaporators 8, 9, 10, the holder 18 is arranged so as to be rotatable relative to the gas supply unit 17.

The interlock arrangement of the invention is described in combination with evaporators with appertaining valves in the exemplary embodiment.

Figure 2:
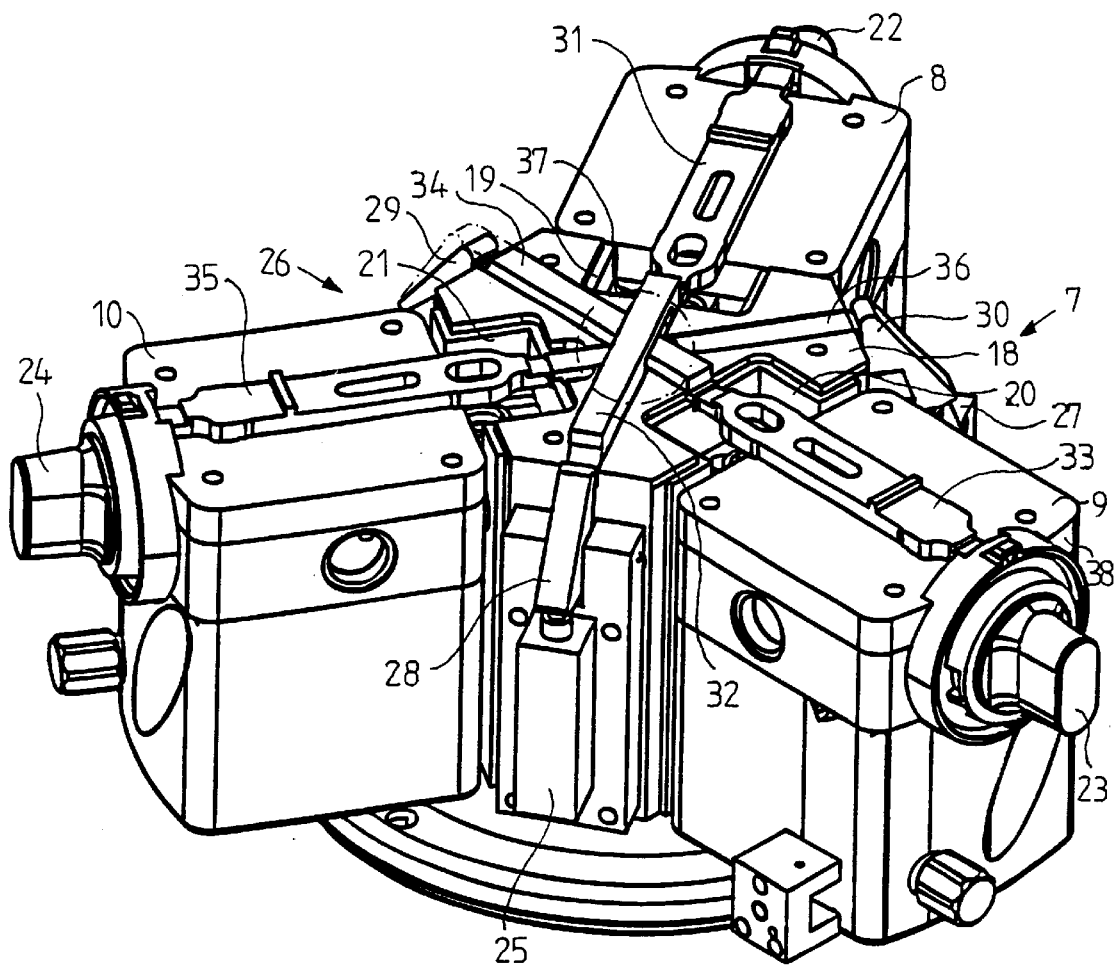
FIG. 2 shows the evaporator carousel according to FIG. 1 in a perspective view, with an interlock arrangement according to the invention.

FIG. 2 shows the evaporator carousel 7 with the gas distributor 18 in an enlarged view compared to FIG. 1. The evaporators 8, 9,10 and the holder 18 are shown without covers in FIG. 2 in order to be able to show the interlock arrangement of the invention. The evaporators 8, 9, 10 are connectable to respective mating recesses 19, 20, 21 that are symmetrically attached to the holder 18. Valve 25, 26, 27 respectively belonging to the evaporators 8, 9,10, are arranged exactly opposite each evaporator 8, 9, 10, the valves 25, 26, 27 being secured in the holder 18 and being provided for controlling the gas flow through the respective evaporator 8, 9, 10 to a patient (not shown) connected to the anesthesia apparatus. The gas conduit system of the anesthesia apparatus, and thus the gas conduit system in the holder 18 between the evaporators 8, 9,10 and the valves 25, 26, 27 is as disclosed in the aforementioned Swedish Patent No. 507 899.

Each valve 25, 26, 27 is provided with a spring-biased lever 28, 29, 30. The respective valves 25, 26, 27 are open in the one position of the respective lever 28, 29, 30 associated therewith and is closed in the other position of the respective lever 28, 29, 30. Each evaporator 8, 9, 10 is connected to one lever 28, 29, 30 of the appertaining valves 25, 26, 27 via slides. Thus, the evaporator 8 is connected to the lever 28 of the valve 25 via slides 31, 32, the evaporator 9 is connected to the lever of the valve 26 via slides 33, 34 and the evaporator 10 is connected to the lever 30 of the valve 27 via slides 35, 36. The paired slides 31 and 32, 33 and 34 and 35 and 36 are arranged in axial alignment with one another. The slides 32, 34, 36 cross in a crossing region 37, and the slides 32, 34, 36 are shaped such that they can be intermeshed with one another in the crossing region 37. The slides 32, 34, 36 are also fashioned in the crossing region 37 so that, as described below, an activation of two or more evaporators is prevented.

Each evaporator 8, 9, 10 is equipped with an adjustment wheel or dial 22, 23, 24 for the activation of the respective evaporator 8, 9, 10 and setting of the desired gas concentration. Upon activation of, for example, the evaporator 9, the adjustment wheel 23 is pressed against the evaporator housing 38 and thereby activates the slide 33, and thus the slide 34 as well, so that they are displaced in their longitudinal directions so that they act on the lever 29 to tilt it into a position that is shown by the dashed lines. In this position, the valve 26, which cannot be seen in FIG. 2, is open. The gas concentration is set by turning the adjustment wheel 23 into the desired position. When turning, the pressed-in position of the adjustment wheel 23 is maintained with known means that are therefore not described in greater detail. In this position, the slide 34 locks the other slides 32 and 36 such that the evaporators 8 and 10 cannot be activated, as described in detail in conjunction with FIGS. 5 and 6. When the adjustment wheel 23 is turned back into a zero position, the slides 33, 34 and the adjustment wheel 23 are moved back into their original positions by the force of the spring-biased lever 29. The lever 29 also returns into its original position and thereby closes the valve 26. A displacement of the respectively appertaining slides and levers ensues in the described way upon activation of the other evaporators 8 and 10, so that only one evaporator can be activated at the same time.

The upper surface of the holder 18 is provided with channels in which the slides 32, 34, 36 are arranged to be displaceable in their respective directions. The channels, which are not shown in FIG. 2, serve the purpose of stabilizing the longitudinal displacement of the slides 32, 34, 36. The slides 31, 33 and 35 are displaceable in channels that are arranged in the aforementioned evaporator covers that are not shown in FIG. 2.

Figure 3:
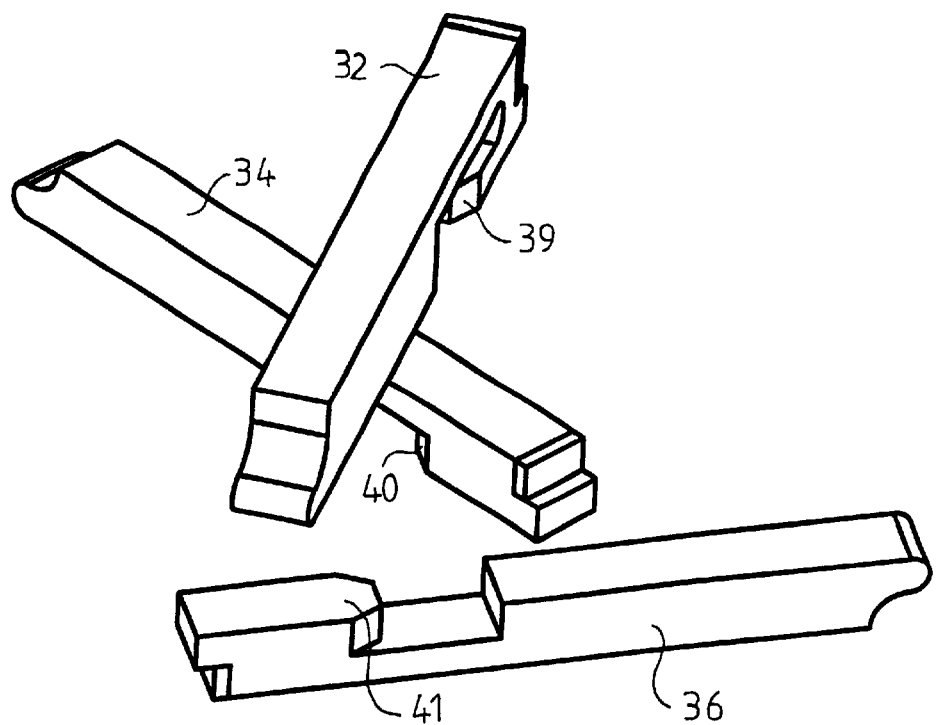
FIG. 3 shows a part of the interlock arrangement according to the invention in an exploded view.

The slides 32, 34, 36 are shown in a disassembled (exploded) form in FIG. 3. As can be seen in FIG. 3 the slides are shaped in the crossing region 37 so that they can be intermeshed with one another. Each slide is provided with a shoulder. Thus, the slide 32 is provided with a shoulder 39, the slide 34 with a shoulder 40 and the slide 36 with a shoulder 41 as shown this FIG. 3.

Figure 4:
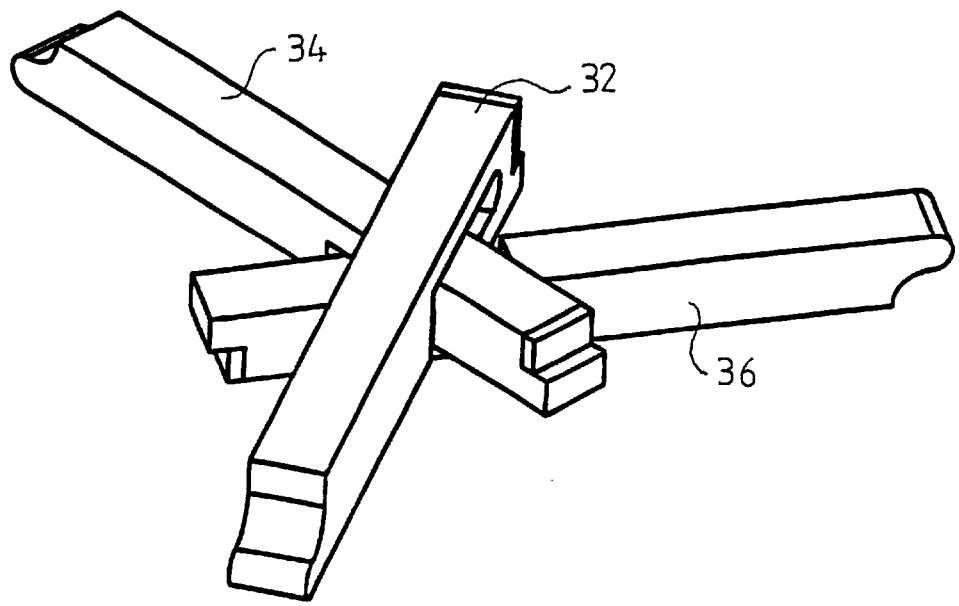
FIG. 4 shows the interlock arrangement according to FIG. 3 in assembled form illustration.

The slides 32, 34, 36 are shown an intermeshed assembly in FIG. 4 and are thus arranged, as in FIG. 1, so that the shoulders 39, 40, 41 (FIG. 3) are attached in a plane in the crossing region 37 (FIG. 2).

Figure 5:
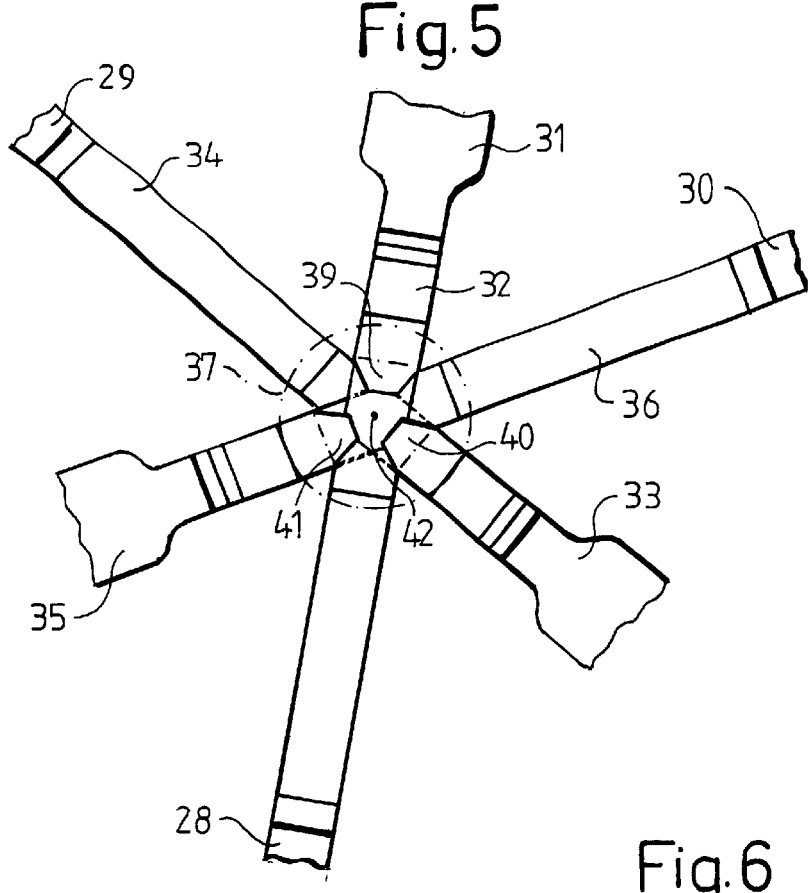
FIG. 5 is plan view of the interlock arrangement according to FIGS. 2, 3 and 4 in a first position.
Figure 6:
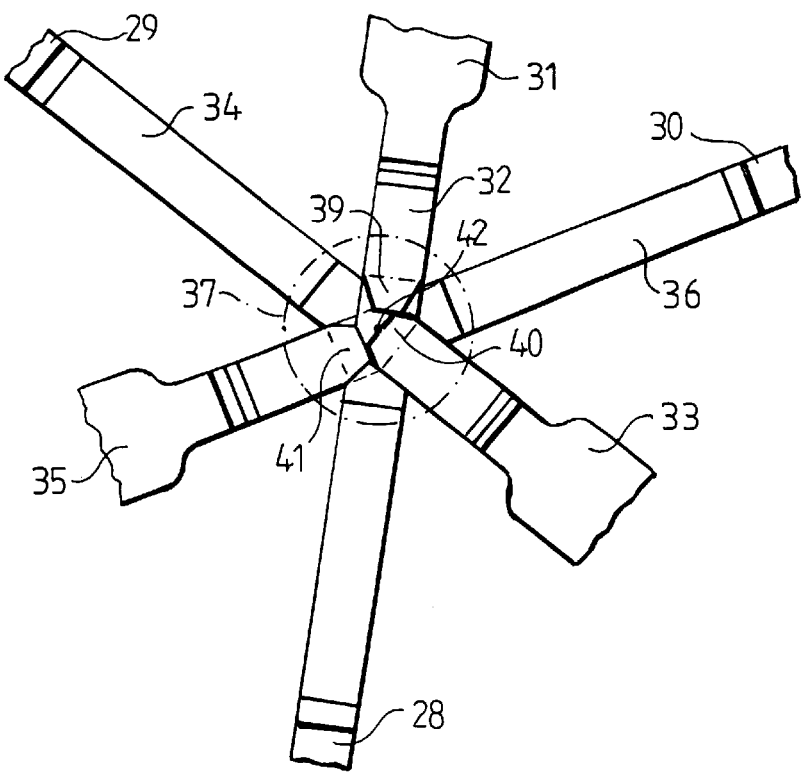
FIG. 6 is plan view of the interlock arrangement according to FIGS. 2, 3 and 4 in a second position.

FIGS. 5 and 6 show the plane of the interlock arrangement in which the shoulders 39, 40, 41 act. As proceeds from FIGS. 5 and 6, the shoulder 39, 40, 41 are trapezoidally fashioned. FIG. 5 shows that the obtuse ends of the shoulders 39, 40, 41 are directed toward an imaginary central point 42 in the crossing region 37. In FIG. 5, the slides 32, 34, 36 with the appertaining shoulders 39, 40, 41 exhibit a position in which none of the evaporators 8, 9, 10 has been activated.

FIG. 6 shows a position of the slide 34 in which the evaporator 9 is activated in the described way. The slide 33, and thus the slide 34, are then displaced in their longitudinal directions and the shoulder 40 is displaced in the direction of the central point 42. In this one limit position, the shoulder 40 blocks the other shoulders 39, 41 and thus also prevents the other slides 32, 35 and 39 from being displaced into an active evaporator/valve position.

The described mechanical elements between the evaporators and valves need not necessarily be formed two successively arranged slides but can instead each be formed by a single long slide.

The procedure described in conjunction with the activation of the evaporator 9 is the same upon activation of the evaporators 8 and 10.

Within the scope of the invention, the holder 18 of the evaporator carousel 7 can be fashioned both for two as well as for more than three evaporators. The interlock arrangement of the invention can, of course, be employed so as to act on some other component instead of a valve. The important function of the interlock arrangement is that only one evaporator is permitted to be activated here at any time.

Although modifications and changes may be suggested by those skilled in the art, it is the intention of the inventor to embody within the patent warranted hereon all changes and modifications as reasonably and properly come within the scope of his contribution to the art.

I claim as my invention:

1. An anesthetic apparatus comprising:
   a plurality of individually activatable anesthetic evaporators connected to a holder and gas distributor;
   a plurality of mechanical elements, each of said evaporators having one of said mechanical elements uniquely associated therewith, said one of said mechanical elements being actuated when the evaporator associated therewith is activated; and
   said plurality of mechanical elements being disposed relative to each other so that all of said mechanical elements cross each other in a crossing region and mechanically interact with each other in said crossing region so that when a mechanical element is actuated, thereby becoming an actuated mechanical element, upon activation of the evaporator associated therewith, the actuated mechanical element blocks actuation of all other mechanical elements in said plurality of mechanical elements, thereby preventing activation of any other evaporator in said plurality of evaporators.

2. An anesthetic apparatus as claimed in claim 1 wherein each of said mechanical elements comprises at least one mechanical slide.

3. An anesthetic apparatus as claimed in claim 2 wherein said slides are mechanically intermeshed with each other in said crossing region.

4. An anesthetic apparatus as claimed in claim 3 wherein each of said slides has a shoulder with each shoulder having an end, the respective shoulders of the respective slides being disposed substantially in a common plane in said crossing region with the respective ends of the respective shoulders facing toward each other.

5. An anesthetic apparatus as claimed in claim 4 wherein said plurality of individually activatable anesthetic evaporators comprises three individually activatable anesthetic evaporators, wherein each said shoulder on each said slide comprises a trapezoidal shoulder and wherein said end of said shoulder comprises an obtuse end, and wherein said slides are intermeshed with each other in said crossing region with the respective obtuse ends of the respective trapezoidal shoulders each being directed toward a central point in said crossing region, each of said slides, when actuated by activation of the evaporator associated therewith, being displaced in a longitudinal direction and causing the shoulder thereof to be displaced toward said central point into a position wherein that shoulder locks all of the other respective shoulders and thereby prevents any other of the slides from being longitudinally displaced.

6. An anesthetic arrangement as claimed in claim 1 wherein the respective evaporators in said plurality of individually activatable anesthetic evaporators are symmetrically radially disposed around said holder and gas distributor.

7. An anesthetic apparatus as claimed in claim 6 wherein the respective mechanical elements in said plurality of mechanical elements are radially symmetrically disposed around said crossing region.

8. An anesthetic apparatus comprising:
   a plurality of anesthetic evaporators connected to a holder and gas distributor;
   a plurality of valves respectively connected between said plurality of evaporators and said holder and gas distributor, said plurality of valves being respectively associated with said plurality of evaporators and each valve having an open state in which the evaporator associated therewith is activated, and a closed state in which the evaporator associated therewith is not activated;
   a plurality of mechanical elements, each of said valves having one of said mechanical elements uniquely associated therewith, said one of said mechanical elements being actuated when the valve associated therewith is in said open state to activate the evaporator associated with the valve in the open state; and
   said plurality of mechanical elements all crossing each other in a crossing region and interacting with each other in said crossing region so that when a mechanical element is actuated, thereby becoming an actuated mechanical element, upon the valve associated therewith being in said open state, the actuated mechanical element blocks actuation of all other mechanical elements, thereby preventing any other valve in said plurality of valves from being in said open state and thereby permitting only one evaporator in said plurality of evaporators from being activated at a time.

9. An anesthesia apparatus as claimed in claim 8 wherein the respective evaporators in said plurality of evaporators and the respective valves in said plurality of valves associated therewith are disposed opposite each other.

10. An anesthetic apparatus as claimed in claim 8 wherein each of said mechanical elements comprises at least one mechanical slide.

11. An anesthetic apparatus as claimed in claim 10 wherein said slides are mechanically intermeshed with each other in said crossing region.

12. An anesthetic apparatus as claimed in claim 11 wherein each of said slides has a shoulder with each shoulder having an end, the respective shoulders of the respective slides being disposed substantially in a common plane in said crossing region with the respective ends of the respective shoulders facing toward each other.

13. An anesthetic apparatus as claimed in claim 12 wherein said plurality of individually activatable anesthetic evaporators comprises three individually activatable anesthetic evaporators, wherein each said shoulder on each said slide comprises a trapezoidal shoulder and wherein said end of said shoulder comprises an obtuse end, and wherein said slides are intermeshed with each other in said crossing region with the respective obtuse ends of the respective trapezoidal shoulders each being directed toward a central point in said crossing region, each of said slides, when actuated by activation of the evaporator associated therewith, being displaced in a longitudinal direction and causing the shoulder thereof to be displaced toward said central point into a position wherein that shoulder locks all of the other respective shoulders and thereby prevents any other of the slides from being longitudinally displaced.

14. An anesthetic arrangement as claimed in claim 8 wherein the respective evaporators in said plurality of individually activatable anesthetic evaporators are symmetrically radially disposed around said holder and gas distributor.

15. An anesthetic apparatus as claimed in claim 14 wherein the respective mechanical elements in said plurality of mechanical elements are radially symmetrically disposed around said crossing region.

* * * * *